United States Patent
Rinner et al.

(10) Patent No.: US 6,551,316 B1
(45) Date of Patent: Apr. 22, 2003

(54) SELECTIVE COMPRESSION AND DISTRACTION INSTRUMENT

(75) Inventors: James A. Rinner, Racine, WI (US); Michael A. Jordan, Racine, WI (US)

(73) Assignee: Beere Precision Medical Instruments, Inc., Kenosha, WI (US)

( * ) Notice: Subject to any disclaimer, the term of this patent is extended or adjusted under 35 U.S.C. 154(b) by 0 days.

(21) Appl. No.: 09/796,410

(22) Filed: Mar. 2, 2001

(51) Int. Cl.⁷ .............................................. A61B 17/66
(52) U.S. Cl. ........................ 606/57; 606/205; 81/427.5; 81/423; 81/352
(58) Field of Search ................................ 606/205–208, 606/53, 57, 90, 99, 105, 55, 58; 600/216, 218, 219, 222; 81/427.5, 423, 352–354, 362

(56) References Cited

U.S. PATENT DOCUMENTS

| | | | |
|---|---|---|---|
| 188,262 A | * | 3/1877 | Russell ........................ 81/353 |
| 427,220 A | * | 5/1890 | Bernard ........................ 81/353 |
| 707,418 A | * | 8/1902 | Howland ..................... 81/338 |
| 2,002,021 A | | 5/1935 | Rouse |
| 3,960,147 A | | 6/1976 | Murray |
| 4,102,339 A | | 7/1978 | Weber |
| 4,271,836 A | | 6/1981 | Bacal |
| 4,502,475 A | | 3/1985 | Weigle |
| 4,898,161 A | | 2/1990 | Grundei |
| 5,245,755 A | | 9/1993 | Krivec |
| 5,297,538 A | | 3/1994 | Daniel |
| 5,529,571 A | | 6/1996 | Daniel |
| 5,885,210 A | | 3/1999 | Cox |
| 5,899,901 A | | 5/1999 | Middelton |
| 6,017,342 A | | 1/2000 | Rinner |
| 6,102,909 A | * | 8/2000 | Chen et al. ................. 606/170 |
| 6,336,387 B1 | * | 1/2002 | Lee ............................ 30/192 |
| 6,386,076 B1 | * | 5/2002 | Swanstrom, Jr. ........... 29/527.1 |

* cited by examiner

Primary Examiner—Kevin Shaver
Assistant Examiner—Michael B. Priddy
(74) Attorney, Agent, or Firm—Arthur J. Hansmann

(57) ABSTRACT

A selective compression and distraction instrument useful in manipulating bone, such as a person's spine during surgery. There are two handle sections and one jaw section. One handle section produces a compression action and the other produces a distraction action. The user determines which action to apply, and then selects the appropriate handle section which is releasably attached to the one jaw section. The jaw section is arranged to have two tips, and the jaw section moves the tips in a parallel relationship toward and away relative to each other. The tips are releasably and interchangeably attachable to the jaw section, and they provide selective spacing of tip blades from each other.

27 Claims, 3 Drawing Sheets

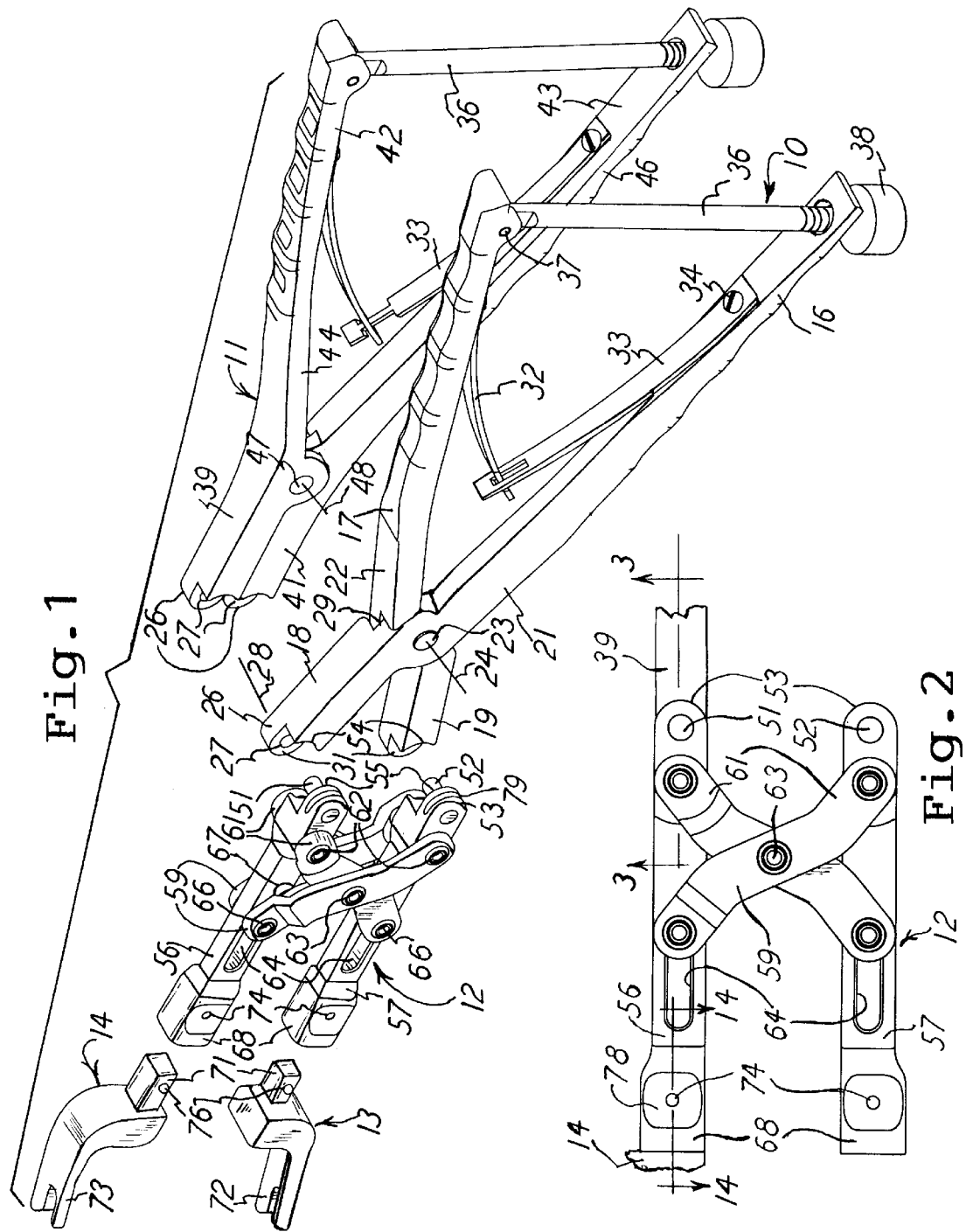

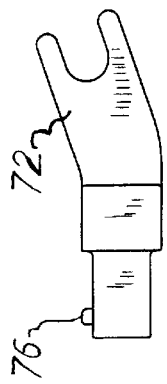
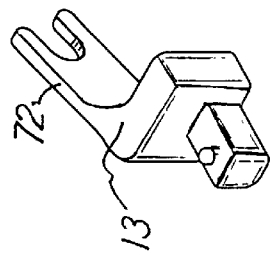
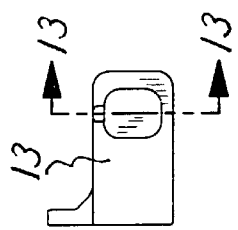
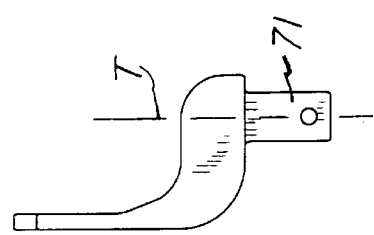
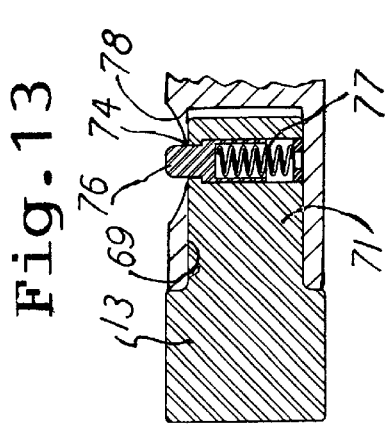
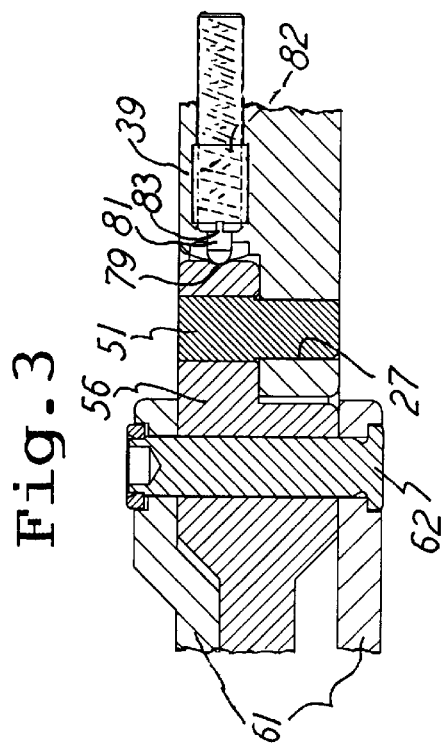

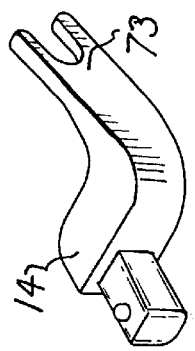
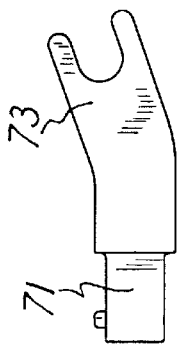
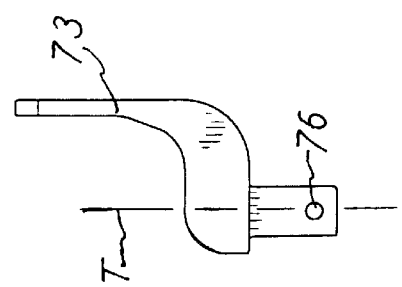
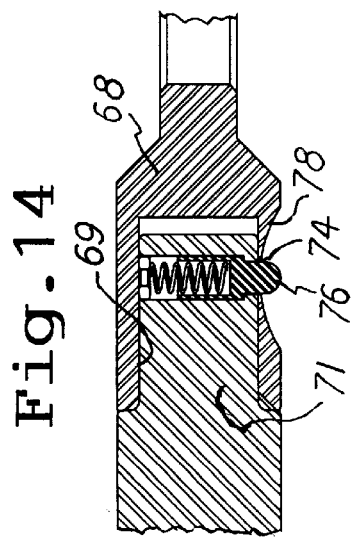
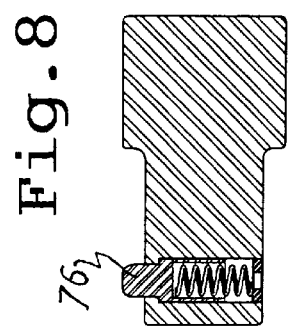

SELECTIVE COMPRESSION AND DISTRACTION INSTRUMENT

This invention relates to a selective compression and distraction instrument which is useful in manipulating bones in a human, particularly in manipulating the spine of a person, such as in surgical procedures. Such manipulation may occur through direct contact of the bone with the instrument, or by devices attached to the bone, such as implants.

BACKGROUND OF THE INVENTION

The prior art is already aware of instruments for compressing and distracting bones or the like, and that prior art is cited herein. Those instruments include a scissors-type arrangement which the user can squeeze to apply the desired force to the bones. One end of each of those instruments has a handle and the opposite end has a jaw for contacting the bones. In one prior art instance, one instrument is useful for both the compression and the distraction force application, and that is shown in my U.S. Pat. No. 6,017,342, entitled Compression and Distraction Instrument.

The present invention provides another instrument arrangement for applying both compression and distraction forces. My aforesaid patent and the present invention both provide for several improvements over the known prior art, and the present invention provides an arrangement wherein surgeons and like users have another variation for the procedure of compressing and distracting bones or other work-pieces. The advantages of my aforesaid patented instrument are also inherent in the present invention.

The instrument of the present invention is in the form of a multi-piece kit which includes two handle sections and one jaw section which is optionally and alternately attached to a selective one of the two handle sections. One handle section is used for compression and the other handle section is used for distraction, so each completed instrument assembly serves its specific purpose and is simplified in configuration.

The selective assembly of either of the two handle sections to a jaw section, as mentioned herein, is quickly and easily accomplished and can be immediately accomplished by the user in the process of preparing the instrument. The attachment of the selected one of the two handle sections results in a sturdy and secure instrument for the required precision of surgery or the like.

Also, the desired action of parallel movement of the bone-engaging jaws is attained by this invention. That is, the two jaws which move relative to each other do so in an orientation wherein the two jaws are and remain in an orientation parallel to each other.

In addition to the one jaw section serving the two handle sections, there are two removably attached jaw tips or fingers which quickly and firmly can be attached to the jaw section itself. Further, those two jaw tips or fingers are releasably attachable in the jaw section and are interchangeable so they can be selectively presented to the work-piece in a plurality of relationships. That is, they can be selectively angularly positioned, variously spaced apart, or like positioning relative to each other and to the handle section itself, all for the user's selected purpose.

The jaws are secured to the jaw section in a connection which is not inadvertently releaseable but instead responds only to an intentional action of releasing. That enhances the appeal of the feature of providing these interchangeable jaws which suit the particularly function being performed.

A method of selectively providing either a compressor or distractor instrument is a part of this invention.

BRIEF DESCRIPTION OF THE DRAWINGS

FIG. 1 is an exploded perspective view of the instrument of this invention.

FIG. 2 is a left side elevational view of a fragment of the showing in FIG. 1.

FIG. 3 is an inverted enlarged section view taken along the plane designated 3—3 on FIG. 2.

FIG. 4 is a perspective view of a tip part seen in FIG. 1.

FIGS. 5, 6, and 7, are right side elevational, left end elevational, and top plan views, respectively, of FIG. 4.

FIG. 8 is an enlarged section view taken along the plane designated 8—8 on FIG. 6.

FIG. 9 is a perspective view of a tip part seen in FIG. 1.

FIGS. 10, 11, and 12 are right side elevational, left end elevational, and top plan views, respectively, of FIG. 9.

FIG. 13 is an enlarged section view taken along the plane designated 13—13 of FIG. 11.

FIG. 14 is an enlarged section view taken along the plane designated 14—14 in FIG. 2.

DETAILED DESCRIPTION OF THE PREFERRED EMBODIMENT AND METHOD

The instrument of this invention is shown in a plurality of sections which include two handle sections 10 and 11 and a jaw section 12. The handle sections 10 and 11 have unique operational actions which differ from each other, and they are separately and alternately releasably attached with the jaw section 12. There is only one jaw section 12 and it has two jaws or tips 13 and 14 releasably attachable thereto, as indicated.

The handle section 10 has two hand-grippable portions 16 and 17 arranged to be squeezed by the surgeon or other user. The handle section 10 also has two jaw portions 18 and 19, and the portions 16 and 18 exist as one integral and elongated piece 21, as shown, and the portions 17 and 19 also exist as one integral and elongated piece 22. Those two pieces 21 and 22 are pivotally joined together by a pivot pin 23 which presents a pivot axis 24.

The ends of the handle jaws 18 and 19 each have a projection 26 which is offset to the right, as viewed in FIG. 1, and each projection 26 presents a pin hole 27 which is disposed with its longitudinal axis parallel to the pivot axis 24, as indicated at 28. It will also be noticed that the two pieces 21 and 22 are nested together to overlap each other, as shown at 29, and they thereby present the two end surfaces 31 of the projections 26 on the center plane which extends along the length of the two pieces 21 and 22.

The handle sections 10 and 11 also have resilient means, such as the leaf springs 32 and 33 which are suitably connected to the handle portions 16 and 17, such as by screws, like the shown screw 34. Thus, in the handle section 10, the handle portions 16 and 17, and likewise with the handle section 11, are spring-urged away from each other. Of course, the user's hand squeezing on the respective handle portions is then against the force of the springs 32 and 33.

Also in each handle section 10 and 11 there is an adjustable limiter tension rod 36 which is pivoted on a pin 37 on the handle portion 17, and there is a nut 38 threadedly engaged with the rod 36 to abut handle portion 16. The respective rods 36 operate against the urging of the springs 32 and 33 and thereby restrict the opening of the handle portions, and that therefore also results in the user being able to set the nut 38 along the rod 36 to thereby retain the position of the handle portions relative to each other, such as portions 16 and 17, and thus retain the position of the respective jaw portions, such as the jaw portions 18 and 19.

The handle sections 10 and 11 differ from each other in that the section 11 has jaw portions 39 and 41 which respectively extend from handle portions 42 and 43. The two portions 39 and 42, and the two portions 41 and 43 respectively form their own single pieces 44 and 46 in the handle section 11. Those two pieces 44 and 46 are pivoted together with a pivot pin 47 extending therethrough and presenting a pivot axis 48. Just as with the heretofore mentioned projections 26, the handle section 11 also has projections 26 and holes 27 and surfaces 31, and the holes 27 on the section 11 have their longitudinal axes parallel to the pivot axis 48, just as with the hole axes 28.

It will now be understood that squeezing the handle portions 16 and 17 toward each other will cause the jaw portions 18 and 19 to move toward each other. That is useful in the compression operation of this instrument. Conversely, squeezing the handle portions 42 and 43 toward each other will cause the jaw portions 39 and 41 to move away from each other. That is useful in the distraction operation of this instrument.

The two handle sections 10 and 11 are complete sub-assemblies in themselves, and they are available for separate and alternate use with the jaw section 12. However, the jaw section 12 is used with both handle sections 10 and 11 in that it is alternately releasably attached to a selected one of the handle sections 10 and 11.

By now it should be understood that both handle sections 10 or 11 are alternately releasably attachable to the jaw section 12. As such, with the use of the handle section 10 there is a compression instrument, and with the use of the handle section 11 there is a distraction instrument.

The sections 10 and 11 are alternately releasably attached to the section 12 by use of the pin holes 27. Thus, the jaw section 12 has laterally projecting pins 51 and 52 which are snugly received in a respective one of the holes 27. Thereby the handles sections 10 or 11 are releasably attached with the jaw section 12, and such attachment and release is achievable by the user at the time of actual use of the instruments. Further, the sections have mating arcuate surfaces 53 and 54 which can slidably contact and support each other and thereby render further stability to the articular pin attachment described herein. Still further, the section 12 has flat surfaces at 55 which contact the flat surfaces 31 for further stability.

The jaw section 12 includes two bars 56 and 57 which are disposed parallel to each other and they always remain so. The pins 51 and 52 are respectively integral with the bars 56 and 57. Links 5.9 and 61 are on each side of the bars 56 and 57, and they are pivotally pinned thereto by pins 62 which extend through the bars 56 and 57. The four links 59 and 61 are also pivotally pinned together by a pin 63 which extends therethrough.

The bars 56 and 57 each have a slot 64 extending therethrough and therealong, and there is a pin 66 respectively extending through the slots 64 and the links 59 and 61. The two pins 66 are slidable in the respective slot 64. The bars 56 and 57 each have a semi-circular cutout 67 facing each other such that upon positioning the bars adjacent each other, the pin 63 is nested in those two cutouts so the bars 56 and 57 can be positioned in contact with each when desired.

The arrangement of the jaw section 12 is such that the parallel bars 56 and 57 move toward and away relative to each other, and they always remain in parallel relationship. That is due to the scissors-like linkage of the jaw section 12 and the presence of the slotted connection between the slots 64 and their respective pins 66.

The end 68 of each bar 56 and 57 has a socket 69 which is flat-sided in cross-section. The two work-piece blades or tips 13 and 14 have ends 71 which are flat-sided and can be of varied cross-sectional shape, as shown, and their cross-sectional shape is the same as that of the sockets 69, and they are respectively snugly received in the matching sockets 69. The tips 13 and 14 also have projecting blade or finger portions 72 and 73 which extend on the instrument when either one of the ends 71 of the tips 13 and 14 is inserted into either one of the sockets 69. The fit is snug, and it is releasable only by the intentional act of the user.

The blades 72 and 73 are offset from a center line T through each tip 13 and 14, and it will be understood that the tips are interchangeable relative to the sockets 69 and thus an amount of offset the blades 72 and 73 can be selected by the user. The distance between the blades 72 and 73 can be selected for the specific work task. The blades 72 and 73 angulate in a second direction, as seen in FIGS. 6 and 10.

Each jaw assembly end 68 has a hole 74 extending into the socket 69, with one hole 74 at one side of each socket 69. A pin 76 is in each tip end 71, and a spring 77 positions the pin 76 to extend outwardly on the ends 71 and the pins 76 therefore nest in the holes 74 in the assembled arrangement, as in FIGS. 13 and 14. In the assembly, the blades 72 and 73 are oriented to extend parallel to each other, and the action of the parallel mechanism 12 causes the blades to remain in parallelism throughout their movement toward and away relative to each other. The force of the blades 72 and 73 on the bone is always in the same direction as the initial contact of the blades on the bone and the blades 72 and 73 will not slip on the bone during the application of force on the bone.

The pin and hole snap connection described is arranged to preclude inadvertent disconnection of the tips 13 and 14 from the jaw assembly 12. It requires a specific manual action of intentionally depressing the pin 76 down and out of the hole 74 for release of the tips 13 and 14 from the jaw section 12. The connection of the tips 13 and 14 in the sockets 69 can be accomplished by depressing the pins 76 while sliding the tip ends 71 into the respective socket.

Removal of the tips 13 and 14 from the jaw section 12 is accomplished only by the provision of a depression 78 in each end 68 and contiguous to the respective hole 74, such as seen in FIGS. 13 and 14. The user can then place a finger into the depression 78 and press down on the pin 76 to release the pin 76 from its entrapment in the hole 74. Only then can the tip 13 and 14 be removed from the jaw section 12, there is no unintentional or accidental release of the tips 13 and 14.

Another spring-loaded pin connection exists at the connection of the handle sections 10 and 11 with the jaw section 12. The ends of the bars 56 and 57 each have a groove or depression 79 which is elongated and arcuate, and those depressions face the handle section 10 or 11 which the user has selected for use. FIG. 3 shows the connection has a pin 81 spring-urged outwardly from the end surface 54 of the handle section by the urging of a spring 82. Each handle jaw portion can be equipped with that spring-loaded pin or ball connection. Thus, when the selected handle section is being assembled with the jaw section 12, they are mated together by sliding relative to the pins 51 and 52 until the spring-loaded pin 81 snaps into the groove 79, thereby securing the assembly until forceful and intentional separation of the two parts is effected. That arrangement with the grooves 79 permits the respective handle jaw portions to pivotally move toward and away from each other while the jaw section bars 56 and 57 remain parallel to each other throughout that handle pivotal movement.

FIG. 3 shows the spring-loaded assembly with the pin 81 and its surrounding housing which can be threadedly connected to the jaw portion. A screwdriver slot 83 is shown to be exposed from the exterior of the jaw portion for the screwing action of the shown housing of the spring-loaded pin 81 into the assembled position with the handle jaw portions. Any manner of effecting a releasable snap connection, such as the one shown in FIG. 3, is suitable.

The invention is to provide an instrument with two handle sections which are arranged in any structural manner to produce compression or distraction action but in the two directions opposite from each other. That is, squeezing one handle section will cause its jaws to open. Squeezing the other handle section will cause its jaws to close. Thus the opposite actions are produced. There is a jaw section which can be of any structure to have it alternately releasably attachable to either handle section. Further, the jaw section may or may not have a parallel action arrangement as described herein. Finally, there may or may not be the tip members releasably attached to the jaw section, those tip members may be included in the jaw section. The details of the method are disclosed herein in conjunction with the description of the construction and the explanation, as revealed herein.

What is claimed is:

1. A selective compressor and distractor instrument comprising:
   a first handle and a second handle with each thereof having two members pivotally joined together at a pivot axis and each of said members having a hand-receptive portion offset to a first side of said pivot axis and arranged to be hand squeezed toward each other and each of said members having a jaw portion extending offset to a second side of said pivot axis in a location opposite from said first side of said axis and with said two members being pivotally joined together for movement of said jaw portions toward and away from each other,
   said jaw portions of said members of said first handle being respectively disposed relative to said hand-receptive portions to move toward each other in response to movement of its said hand-receptive portions toward each other, and said jaw portions of said members of said second handle being respectively disposed relative to its said hand-receptive portion to move away from each other in response to movement of its said hand-receptive portion toward each other,
   a parallel-action assembly of a plurality of links having a pivot axis where said links are pivotally joined together and having a first two ends disposed offset to a first side of said assembly pivot axis and said links having a second two ends disposed offset to a second side of said assembly pivot axis in a location opposite from said first side of said assembly pivot axis and being disposed in an orientation parallel to each other and with said links being connected together to provide parallel movement of said second two ends toward and away from each other upon pivotal action of said assembly,
   pivotal connectors releasably interengaged between said assembly first two ends and said handle jaw portions of a selected one of said first handle and said second handle, and
   a work-piece engagable member on each of said assembly second two ends for parallel movement toward and away from each other in accord with the parallel movement of said assembly second two ends.

2. The selective compressor and distractor instrument as claimed in claim 1, wherein:
   each said work-piece engagable member is friction-releasable from said assembly second two ends.

3. The selective compressor and distractor instrument as claimed in claim 1, including:
   each said work-piece member has a center line and includes a work-piece contacting prong which is offset from said center line, and
   each said work-piece member includes a portion which engages each of said assembly second two ends in alterable arrangements whereby said prong is selectively positionable relative to said center line at selectively varying locations relative to said center line.

4. The selective compressor and distractor instrument as claimed in claim 3, wherein:
   each said work-piece member portion and said assembly have interengageable flat-sided interconnectors thereon which are arranged for selectively interchangeable interconnection orientation with said assembly two ends.

5. The selective compressor and distractor instrument as claimed in claim 4, including
   said interconnectors have overlapping inner and outer portions, and
   a spring-urged pin assembly on said inner portion and having a pin extending into said outer portion within the outer dimensional limits of said outer portion.

6. A method of arranging an instrument for selectively applying compression and distraction forces, comprising the steps of:
   pivotally assembling a work-piece jaw having a pivot axis and a first two portions on one side of said axis and movable relative to each other in equal distances in a plane transverse to said pivot axis and having a second two portions on a side of said axis opposite from said one side and movable relative to each other in said plane and identical to a direction and amount of said equal distance movements,
   providing a work-piece engaging member at each of said second two portions, and
   releasably connecting to said first two portions a selected one of two handles which are individually pivoted together and which each have two jaw portions that respectively move toward or away from each other, and opposite to each other, in response to squeezing said handles.

7. The method of arranging an instrument for selectively applying compression and distraction forces, as claimed in claim 6, wherein:
   said releasably connecting step is accomplished with a pin connection which is connectable and disconnectable between said jaw first two portions and said selected one of said two handles by having a pin positioned into a pin opening.

8. The method of arranging an instrument for selectively applying compression and distraction forces, as claimed in claim 7, including:
   said work-piece engaging members each having a central axis,
   providing two work-piece engaging surfaces on each said work-piece engaging member and faced away from each other and being offset relative to said central axis, and releasably attaching said work-piece engaging members in a manner to be interchangeable relative to said second two portions and about said central axis to thereby present selectively different work-piece engaging surfaces to a work-piece.

9. A selective compressor and distractor instrument comprising:
   a three-piece collection of pivotal members distinct from each other in construction,
   one of said members being a jaw member having a work-piece end and a force-receptive end,
   the other two of said members being handle members with each thereof having a pivot axis and hand-grippable portions located to a first side of said pivot axis and jaw member connectable portions located to a second side of said pivot axis opposite from said first side,
   said jaw member connectable portions on a first one of said handle members being disposed relative to said pivot axis and said hand grippable portions to move toward each other in response to moving said handle grippable portions of said first handle member toward each other, and said jaw member connectable portions on a second one of said handle members being disposed relative to said pivot axis and said hand grippable portions to move away from each other in response to moving said handle grippable portions of said second handle member toward each other, and
   a releasable connection interengaged between said jaw member and said jaw member force-receptive end connectable portions and said connection being arranged to accommodate releasable attachment of a selected one of said handle members with said jaw member for selective compression and distraction.

10. The selective compressor and distractor instrument as claimed in claim 9, wherein:
    said jaw member includes a plurality of links pivotally connected together and having two of said links serving as the connection between said handle and jaw member and with said two links being movable in parallel orientation relative to each other.

11. The selective compressor and distractor instrument as claimed in claim 10, including:
    a work-piece attachment releasably attached to said jaw member and having offset blades and arranged for interchangeable attachment relative to said jaw member to present selective portions of said blades to the work piece.

12. The selective compressor and distractor instrument as claimed in claim 11, including:
    a spring loaded connector interposed between said work piece work piece attachment and said jaw member and providing the releasable attachment therebetween.

13. The selective compressor and distractor instrument as claimed in claim 9, wherein:
    said jaw member has a plurality of links pivoted together to have said work-piece end arranged in two portions extending parallel to each other and movable toward and away from each other, and
    said jaw member links are pivoted together and arranged to present said work-piece two portions for maintaining the parallel relationship throughout pivotal movement.

14. A selective compressor and distractor instrument comprising:
    a kit having two handles and one jaw pivotal assembly selectively releasably attached to either of said handles,
    said jaw pivotal assembly having two work-piece engaging surfaces facing each other and having two work-piece engaging surfaces facing away from each other and with the respective two of said surfaces being movable toward and away from each other upon pivot action of said assembly,
    each of said two handles having two elongated members pivoted together about a pivot axis and having two grippable portions squeezable toward each other, and
    each two of said elongated members having two jaw portions movable in response to squeezing of said two grippable portions toward each other and with said jaw portions being disposed relative to said pivot axis to have said two jaw portions on a first one of said handles move toward each other for compression of a work-piece by said jaw pivotal assembly surfaces in response to the squeezing and to have said two jaw portions on a second one of said handles move away from each other for distraction of a work-piece by said jaw pivotal assembly in response to the squeezing.

15. The compressor and distractor instrument as claimed in claim 14, including:
    jaw members attached to and separable from said assembly and having said work-piece surfaces thereon and being selectively attached in said assembly and arranged to present selective pairs of said surfaces in selective facing positions relative to facing toward and away from each other.

16. The compressor and distractor instrument as claimed in claim 15, wherein:
    said jaw members each have a central axis extending parallel to said surfaces and with said surfaces offset from said central axis and with said jaw members being interchangeably attachable in said assembly to have said surfaces selectively offset from said central axis in selective distances.

17. A compressor and distractor instrument kit comprising:
    a three-piece kit including two handles and one jaw member,
    each of said handles having two handle-squeezable portions and two jaw portions which respectively move toward and away from each other in response to squeezing of said handle-squeezable portions,
    said two handles having constructions different from each other and being arranged whereupon squeezing said handle-squeezable portions of one of said handles causes the respective said jaw portions to move towards each other and squeezing said handle-squeezable portions of the other of said handles causes the respective said law portions to move away from each other, and
    said jaw member and each said two handles having releasable interconnectors selectably and alternately engageable between said handles and said jaw member.

18. The compressor and distractor instrument kit as claimed in claim 17, including:
    two jaw tips releasably attachable to said jaw member for engaging a work piece upon compression or distraction action of said instrument.

19. The compressor and distractor instrument kit as claimed in claim 18, including:
    a spring and a spring-urged member providing releasable attachment between said jaw tips and said jaw member, and
    said spring-urged member being completely disposed within the exterior confines of said jaw member to thereby preclude inadvertent depressing of said spring-urged member against said spring and thereby cause inadvertent release of said tip from said jaw member.

20. The compressor and distractor instrument kit as claimed in claim 17, including:
   said jaw member being an assembly of links pivotally pinned together and including two spaced-apart links disposed in an orientation parallel to each other and with said assembly being pivotally arranged to have said two links remain parallel to each other during all said toward and away movement.

21. The compressor and distractor instrument kit as claimed in claim 20, including:
   said releasable interconnectors being pivotal interconnectors and having a spring-loaded pin and slot interengaged combination therebetween for relative pivotal movement between said jaw member and the selected one of said handles and with the pivotal movement being in a plane, and
   said slot extending along a direction parallel to said plane for accommodating the parallel movement of said two links.

22. A compressor and distractor instrument kit for forcing on bone in surgical operations comprising:
   a pivotal handle section being squeezable to a pivoted closed position and being spring-biased to a pivoted open position and having a jaw portion with two connection areas with each thereof having an axis extending therethrough and with each thereof being arranged for pivotal open and closed movement of said connection areas selectively toward and away from each other upon alternate squeezing and releasing of said handle section,
   two jaw tips releasably connected to respective ones of said connection areas and extending along each respective axis thereof and being movable toward and away from each other in response to the pivotal movement of said connection areas and having blades thereon for contacting bone for applying force to the bone,
   the releasable connection between said jaw tips and said connection areas being a telescopic connection with said tips being movable along said axis for connecting and disconnecting said tips relative to said connection areas, and
   said telescopic connection has identical flat-sided surfaces on said jaw tips and said jaw portion and with said surfaces being in contact with each other and extending parallel to the extent of said axis and being arranged to preclude rotation of said jaw tips relative to said jaw portion.

23. The compressor and distractor instrument kit for forcing on bone in surgical operations as claimed in claim 22, including:
   a spring and a spring-urged member providing the releasable connection between said jaw tips and said jaw portion, and
   said spring-urged member being completely disposed within the exterior confines of said jaw portion to thereby preclude inadvertent depressing of said spring-urged member against said spring and thereby cause inadvertent release of said jaw tip from said connection areas.

24. The compression and distraction instrument kit for forcing on bone in surgical operations as claimed in claim 22, including:
   the releasable connection between said jaw tips and said connection areas being arranged to have said jaw tips interchangeably positioned between said two areas,
   a blade portion on each said jaw tip and extending thereon in a location offset from said axis and at a first spaced-apart distance from each other and whereby the interchanging of said jaw tips between said areas presents said blade portions at a second spaced-apart distance from each other and different from said first distance.

25. A method of selectively effecting an instrument for use in forcing on bone, comprising the steps of:
   pivotally assembling a work piece jaw having two spaced-apart ends disposed extending in respective two planes which are parallel to each other,
   arranging said jaw for movement of said ends toward and away relative to each other and only in the parallel relationship throughout the movement,
   applying a handle to said jaw for effecting the movement of said ends, and
   providing a jaw tip arranged to be releasably attachable to each respective one of said ends for contact of the bone for forcing onto the bone.

26. The method of selectively effecting an instrument for use in forcing on bone as claimed in claim 25, including the step of:
   arranging said jaw ends and said tips to be interchangeable whereby either said jaw tip can be attached to either said end.

27. The method of selectively effecting an instrument for use in forcing on bone as claimed in claim 26, including the step of:
   positioning bone contacting blades on said tips in locations offset thereon whereby the interchange of said tips effects selective spacing apart of said blades from each other.

* * * * *